(12) United States Patent
Herleikson (10) Patent No.: US 9,833,632 B2
(45) Date of Patent: Dec. 5, 2017

(54) SYNCHRONIZED CARDIOVERSION MIXED MODE OPERATION AND TIMING VERIFICATION

(71) Applicant: KONINKLIJKE PHILIPS N.V., Eindhoven (NL)

(72) Inventor: Earl Clark Herleikson, Cinebar, WA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/897,660

(22) PCT Filed: Jun. 10, 2014

(86) PCT No.: PCT/IB2014/062091
§ 371 (c)(1),
(2) Date: Dec. 11, 2015

(87) PCT Pub. No.: WO2014/199291
PCT Pub. Date: Dec. 18, 2014

(65) Prior Publication Data
US 2016/0121132 A1    May 5, 2016

Related U.S. Application Data

(60) Provisional application No. 61/833,464, filed on Jun. 11, 2013.

(51) Int. Cl.
*A61N 1/39*    (2006.01)
*A61B 5/0245*    (2006.01)
*A61B 5/0452*    (2006.01)

(52) U.S. Cl.
CPC .......... *A61N 1/3987* (2013.01); *A61B 5/0245* (2013.01); *A61B 5/0452* (2013.01); *A61N 1/395* (2013.01); *A61N 1/3925* (2013.01)

(58) Field of Classification Search
CPC .. A61B 5/0456; A61N 1/3987; A61N 1/3925; A61N 1/39
See application file for complete search history.

(56) References Cited

U.S. PATENT DOCUMENTS

3,832,994 A    9/1974 Richer et al.
3,952,750 A    4/1976 Mirowski et al.
(Continued)

*Primary Examiner* — George Evanisko (57) ABSTRACT

A defibrillator system employs an external ECG monitor (40) and a defibrillator (20). In operation, external ECG monitor (40) generates a synchronized cardioversion input signal as one of an external ECG waveform (50) of a heart (11) of a patient (10) or an external synchronized pulse (51) indicative of a detection by the external ECG monitor (40) of at least one QRS complex of the external ECG waveform (50). Defibrillator (40) includes a synchronized cardioversion input channel (29) for receiving the synchronized cardioversion input signal from external ECG monitor (40), and controls a conditional delivery of a defibrillation shock synchronized with the synchronized cardioversion input signal to the patient (10) in response to the defibrillator (20) receiving the synchronized cardioversion input signal. One condition for shock delivery is a measured time delay between an internal ECG waveform (30) and the synchronized cardioversion input signal being less than a baseline time delay.

20 Claims, 3 Drawing Sheets

(56) References Cited

U.S. PATENT DOCUMENTS

| | | | |
|---|---|---|---|
| 4,635,639 A | * | 1/1987 | Hakala ............... A61N 1/36014 |
| | | | 600/509 |
| 5,105,821 A | * | 4/1992 | Reyes ..................... A61N 1/39 |
| | | | 600/508 |
| 5,758,654 A | | 6/1998 | Burton-Krahn et al. |
| 5,819,007 A | | 10/1998 | Elghazzawi |
| 6,591,135 B2 | | 7/2003 | Palmer et al. |
| 7,072,709 B2 | | 7/2006 | Xue |
| 7,085,601 B1 | | 8/2006 | Bardy et al. |
| 7,640,055 B2 | | 12/2009 | Geva et al. |
| 2007/0255150 A1 | | 11/2007 | Brodnick |

\* cited by examiner

SYNCHRONIZED CARDIOVERSION MIXED MODE OPERATION AND TIMING VERIFICATION

This application is a national stage application under 35 U.S.C. §371 of International Application No. PCT/IB2014/062091 filed on Jun. 10, 2014 and published in the English language on Dec. 18, 2014 as International Publication No. WO 2014/199291 A1, which claims priority to U.S. Application No. 61/833,464 filed on Jun. 11, 2013, the entire disclosures of which are incorporated herein by reference.

The present invention generally relates to a synchronized cardioversion mode of a defibrillator. The present invention specifically relates to the synchronized cardioversion mode of the defibrillator providing (1) a mixed mode operation involving an external ECG monitor communicating a synchronized cardioversion input signal in the form of an ECG waveform or a synchronized pulse, and (2) a timing verification preventing an excessive time delay between an internal ECG waveform and the synchronized cardioversion input signal for purposes of executing a synchronized cardioversion.

Historically, synchronized cardioversion has been used to stop atrial fibrillation of a patient's heart. Specifically, during atrial fibrillation, ventricles of the patient's heart are continuing to contract, which produces an organized heartbeat that is capable of sustaining the patient's life. Nonetheless, atrial fibrillation typically results in an erratic heat rhythm and a failure to stop atrial fibrillation allows blood to pool in the atria of the heart, which can lead to blood clots that can further lead to a stroke.

A synchronized cardioversion method of terminating atrial fibrillation is with a defibrillation shock to the patient's heart that is synchronized with contractions of the ventricles in order to minimize risk that the defibrillation shock could cause ventricular fibrillation of the patient's heart, which is not capable of sustaining the patient's life. More particularly, without synchronization of the defibrillation shock to a QRS complex, the atrial defibrillation shock may occur during the repolarization of the ventricles resulting in ventricular fibrillation. Consequently, the synchronized cardioversion shock should be delivered within sixty (60) milliseconds a peak of the QRS complex in order to avoid the possibility of delivering the atrial defibrillation shock on a T-wave.

Defibrillators today usually have the capability to measure ECG directly from the patient and detect the QRS signal internally, and to deliver a synchronized cardioversion shock based on this signal. However, there are times where the clinician will prefer to use an external ECG monitor to monitor the patient and provide a signal to the defibrillator that is then used to synchronize the shock. The external ECG monitor may either supply a high level ECG analog output signal to a ECG input channel or it may supply a high level synchronizing pulse output signal to a synchronized cardioversion input channel. Regardless of the type of output signal, as previously stated, the synchronized cardioversion shock should be delivered within sixty (60) milliseconds a peak of the QRS complex in order to avoid the possibility of delivering the atrial defibrillation shock on a T-wave. Consequently, a time delay for delivering the shock is divided between the external ECG monitor and the defibrillator.

For example, with the output being a high level synchronizing pulse and a 60 milliseconds window, the external ECG monitor is allowed 35 milliseconds to perform R-wave detection and provide the high level synchronizing pulse to the defibrillator. The defibrillator is then allowed 25 milliseconds to receive this pulse and deliver the synchronized cardioversion shock. However, there is a safety risk that the clinician may connect a high level synchronizing pulse output of the external ECG monitor to the ECG input channel of the defibrillator that is expecting a high level ECG input signal. For this scenario, the external ECG monitor is detecting the QRS complex with time delay associated with this detection that can be as high as 35 milliseconds. The defibrillator is expecting ECG data but instead is processing the high level synchronizing pulse for QRS detection. The defibrillator is not set up to properly analyze a high level synchronizing pulse for QRS detection. Thus, there is a safety risk to the patient.

On the other hand, the clinician may connect a high level ECG output from the external ECG monitor to the synchronizing cardioversion input of the defibrillator. A defibrillator that is expecting a high level synchronizing pulse is not set up properly to analyze ECG data and correctly detect the QRS. This configuration is also a safety risk to the patient.

The present invention allows the clinician to connect either signal to the same input channel of the defibrillator by using an algorithm to discriminate between the two types of signals and processing the signals according to the type of signal. Specifically, if the signal is an ECG analog output of an external ECG monitor, then the defibrillator will use a QRS detection algorithm to trigger the synchronized pulse. Conversely, if the signal is the synchronizing pulse output of the external ECG monitor, then the defibrillator will detect this pulse with minimal time delay to trigger the synchronized pulse without the use of a QRS detection algorithm. Consequently, a risk that the clinician may incorrectly configure synchronized cardioversion on the defibrillator using an external ECG monitor is minimized, if not eliminated. Additionally, the present invention minimizes, if not eliminates, the risk that the clinician can incorrectly deliver a shock on a T-wave resulting in ventricular fibrillation when using an external ECG monitor output for synchronizing the shock by alerting the clinician if the time delay from the external ECG monitor is excessive.

One form of the present invention is a method for a synchronized cardioversion operation by a defibrillator. The method involves the defibrillator receiving a synchronized cardioversion input signal from an external ECG monitor through an synchronized cardioversion input channel, wherein the synchronized cardioversion input signal is one of external ECG waveform of a heart of a patient or an external synchronized pulse indicative of a detection by the external ECG monitor of at least QRS complex of the external ECG waveform. The method further involves the defibrillator conditionally delivering a defibrillation shock synchronized with the synchronized cardioversion input signal to the patient in response to the defibrillator receiving the synchronized cardioversion input signal.

Conditions for delivering the defibrillation shock to the patient include, but are not limited, to (1) the defibrillator receiving and detecting the synchronized cardioversion input signal is the external ECG waveform and detecting at least one QRS complex within the external ECG waveform, particularly without any excessive time delay due to the defibrillator receiving the external ECG waveform and detecting the at least one QRS complex, and (2) the defibrillator receiving and detecting the synchronized cardioversion input signal is the synchronized pulse, particularly without any excessive time delay for the defibrillator in receiving and detecting the synchronized pulse.

A second form of the present invention is defibrillator for synchronized cardioversion employing a shock source and a controller. In operation, the controller receives a synchronized cardioversion input signal from an external ECG monitor through a synchronized cardioversion input channel, wherein the synchronized cardioversion input signal is one of an external ECG waveform of heart of a patient or an external synchronized pulse indicative of a detection by the external ECG monitor of at least one QRS complex of the external ECG waveform. The controller further controls a conditional delivery of a defibrillation shock synchronized with the synchronized cardioversion input signal by the shock source to the patient in response to the controller receiving the synchronized cardioversion input signal.

Conditions for delivering the defibrillation shock to the patient include, but are not limited, to (1) the controller receiving and detecting the synchronized cardioversion input signal is the external ECG waveform and detecting at least one QRS complex within the external ECG waveform, particularly without any excessive time delay due to the controller receiving the external ECG waveform and detecting the at least one QRS complex, and (2) the controller receiving and detecting the synchronized cardioversion input signal is the synchronized pulse, particularly without any excessive time delay for the controller in receiving and detecting the synchronized pulse.

A third form of the present invention is defibrillation system for synchronized cardioversion employing an external ECG monitor and a defibrillator. In operation, the defibrillator receives a synchronized cardioversion input signal from the external ECG monitor through a synchronized cardioversion input channel, wherein the synchronized cardioversion input signal is one of external ECG waveform of heart of a patient or an external synchronized pulse indicative of a detection by the external ECG monitor of at least one QRS complex of the external ECG waveform. The defibrillator further controls a conditional delivery of a defibrillation shock synchronized with the synchronized cardioversion input to the patient in response to the defibrillator receiving the synchronized cardioversion input.

Conditions for delivering the defibrillation shock to the patient include, but are not limited, to (1) the defibrillator receiving and detecting the synchronized cardioversion input signal is the external ECG waveform and detecting at least one QRS complex within the external ECG waveform, particularly without any excessive time delay due to the defibrillator receiving the external ECG waveform and detecting the at least one QRS complex, and (2) the defibrillator receiving and detecting the synchronized cardioversion input signal is the synchronized pulse, particularly without any excessive time delay for the defibrillator in receiving and detecting the synchronized pulse.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

For purposes of the present invention, the terms "synchronized cardioversion" "unsynchronized cardioversion", "cardiac cycle", "QRS complex", "P-wave", "Q-wave", "R-wave", "S-wave", "T-wave", "QT interval", "electrode pad/paddle" and "electrocardiogram ("ECG")", "monitor", "source", "detector" and "discharger" as well as synonymous and related terms are to be broadly interpreted as known in the art of the present invention.

To facilitate an understanding of the present invention, exemplary embodiments of the present invention will be provided herein directed to a mixed mode operation and timing verification of a defibrillator in a synchronized cardioversion mode.

Figure 1:
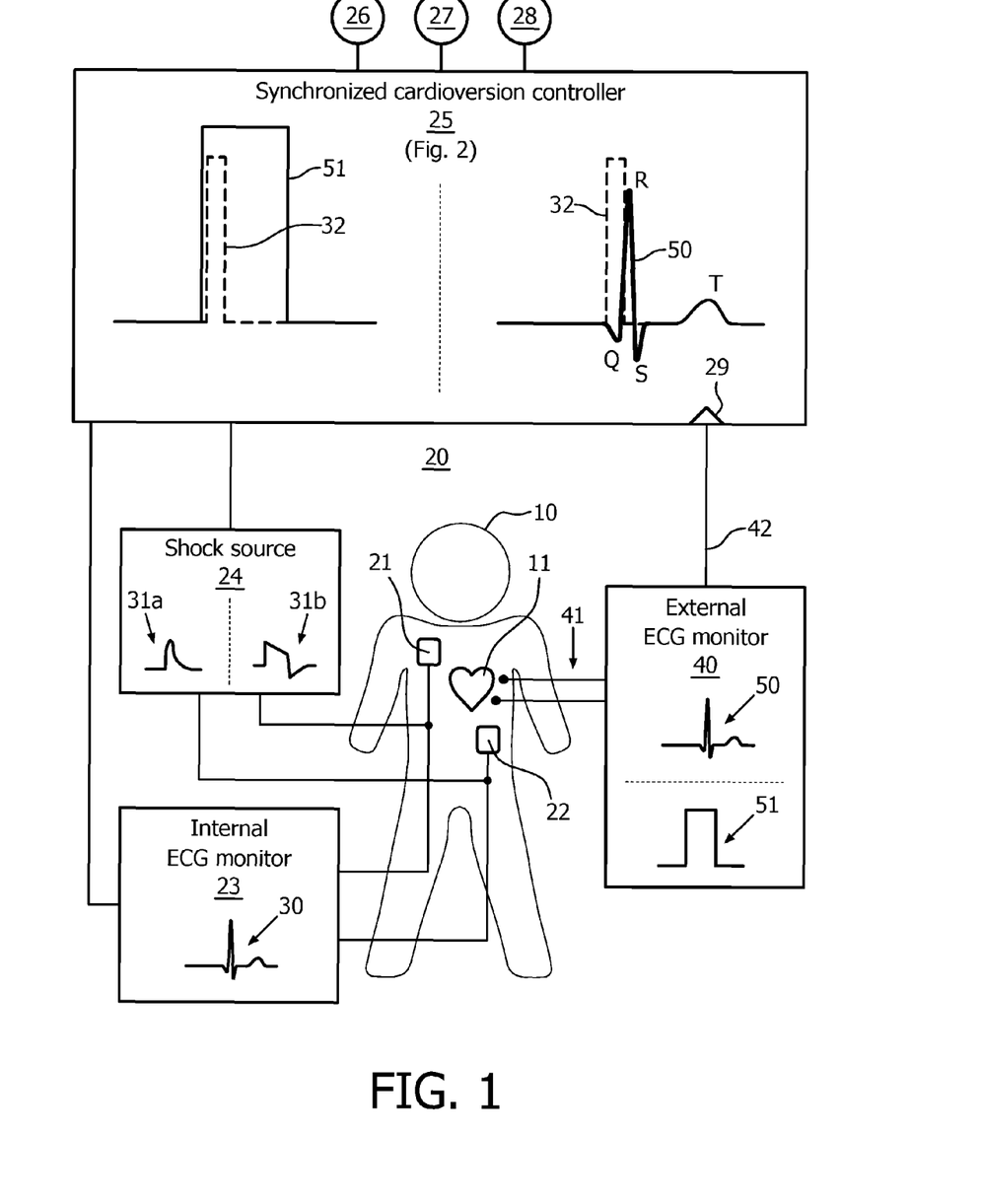
FIG. 1 illustrates an exemplary embodiment of a defibrillator with a mixed mode/timing verification synchronized cardioversion capabilities in accordance with the present invention.

Referring to FIG. 1, a defibrillator 20 of the present invention employs a pair of electrode pads or paddles 21 and 22, optional ECG leads (not shown), a ECG monitor 23 (internal or external), a shock source 24, and a synchronized cardioversion controller 25.

Electrode pads or paddles 21 and 22 are structurally configured as known in the art to be conductively applied to a patient 10 in an anterior-apex arrangement as shown in FIG. 1 or in an anterior-posterior arrangement (not shown). Electrode pads or paddles 21 and 22 conduct a defibrillation shock from shock source 24 to a heart 11 of patient 10 and conduct electrical activity of heart 11 of patient 10 to ECG monitor 23. Alternatively or concurrently, ECG leads as known in the art may be connected to patient 10 to conduct the electrical activity of heart 11 of patient 10 to ECG monitor 23.

ECG monitor 23 is structurally configured as known in the art to measure an ECG waveform 30 of heart 11 of patient 10 as an indication patient 10 is experiencing an organized heartbeat condition or an unorganized heartbeat condition. An example of ECG waveform 30 indicating an organized heartbeat condition is an ECG waveform 30 without a P-wave that is representative of an organized contraction of the ventricles of heart 11 being capable of pumping blood.

In one embodiment, ECG monitor 23 employs a digital signal processor (not shown) for streaming ECG waveform data to controller 25.

Shock source 24 is structurally configured as known in the art to store electric energy for delivery of a defibrillation shock 31 via electrode pads/paddles 21 to heart 11 of patient 10 as controlled by controller 25. In practice, defibrillation shock 31 may have any waveform as known in the art. Examples of such waveforms include, but are not limited to, a monophasic sinusoidal waveform (positive sine wave) 31$a$ and a biphasic truncated waveform 31$b$ as shown in FIG. 1.

In one embodiment, shock source 24 employs a high voltage capacitor bank (not shown) for storing a high voltage via a high voltage charger and a power supply upon a pressing of a charge button 26. Shock source 24 further employs a switching/isolation circuit (not shown) for selectively applying a specific waveform of an electric energy charge from the high voltage capacitor bank to electrode pads/paddles 21 as controlled by controller 25.

Controller 25 is structurally configured to execute a synchronized cardioversion in conjunction with an external ECG monitor 40 connected via a sync cable 42 to an ECG input channel 29 of controller 25.

External ECG monitor 40 is structurally configured to measure ECG waveform data of heart 11 of patient 10 as known in the art via a ECG lead set 41 conductively attached to patient 10. External ECG monitor 40 communicates a synchronized cardioversion input signal to controller 25 as one of external ECG waveform 50 of patient 10 or a synchronized pulse 51 indicative of a detection by external ECG monitor 40 of a QRS complex within the ECG waveform 50.

Controller 25 is structurally configured to utilize a pulse profile 32 for detecting whether the synchronized cardioversion input signal from external ECG monitor 40 via sync cable 42 is external ECG waveform 50 or synchronized pulse 51. Specifically, pulse profile 32 has an amplitude, a rise time and/or a duration defining a baseline synchronized pulse signal. An equivalence of synchronized cardioversion input signal to pulse profile 32 is interpreted by controller 25 as synchronized pulse signal 51 from an external ECG monitor 40. Conversely, a nonequivalence of synchronized cardioversion input signal to pulse profile 32 is interpreted by controller 25 as a ECG input signal 50 from an external ECG monitor 40. In practice, the equivalence and nonequivalence of synchronized cardioversion input signal will be dependent upon a designed functionality of defibrillator 20 and external ECG monitor 40 that must be able to distinguish between the external ECG waveform and the synchronizing pulse. In one embodiment, equivalence is defined as the synchronized cardioversion input signal having an amplitude, a rise time and a duration equal to greater than the respective amplitude, rise time and duration of the baseline synchronized pulse signal.

Controller 25 is also structurally configured to compare a baseline time delay to a measured time delay between an internal monitoring of a ECG waveform via internal ECG input monitor 23 and a reception and detection of the synchronizing cardioversion input signal via input channel 29 for determining whether a time delay between an internal ECG waveform 30 and the synchronizing cardioversion input signal is or is not excessive. In practice, the baseline time delay is preferably derived at a minimum from a sixty (60) millisecond window for external ECG monitor 40 to generate and communicate the synchronized cardioversion input signal to controller 25 and for controller 25 to detect the input signal and deliver the synchronized cardioversion shock.

Also in practice, the measurement points of internal ECG waveform 30 and the synchronized cardioversion input signal are preferably the synchronized points for a defibrillation shock.

In one embodiment, controller 25 employ hardware/circuitry (e.g., processor(s), memory, etc.) for executing a synchronized cardioversion method of the present invention installed as software/firmware within controller 25. In practice, the software/firmware may employ a QRS detector and a shock discharger as known in the art that are modified or revised to support an execution of the synchronized cardioversion method of the present invention.

Figure 2:
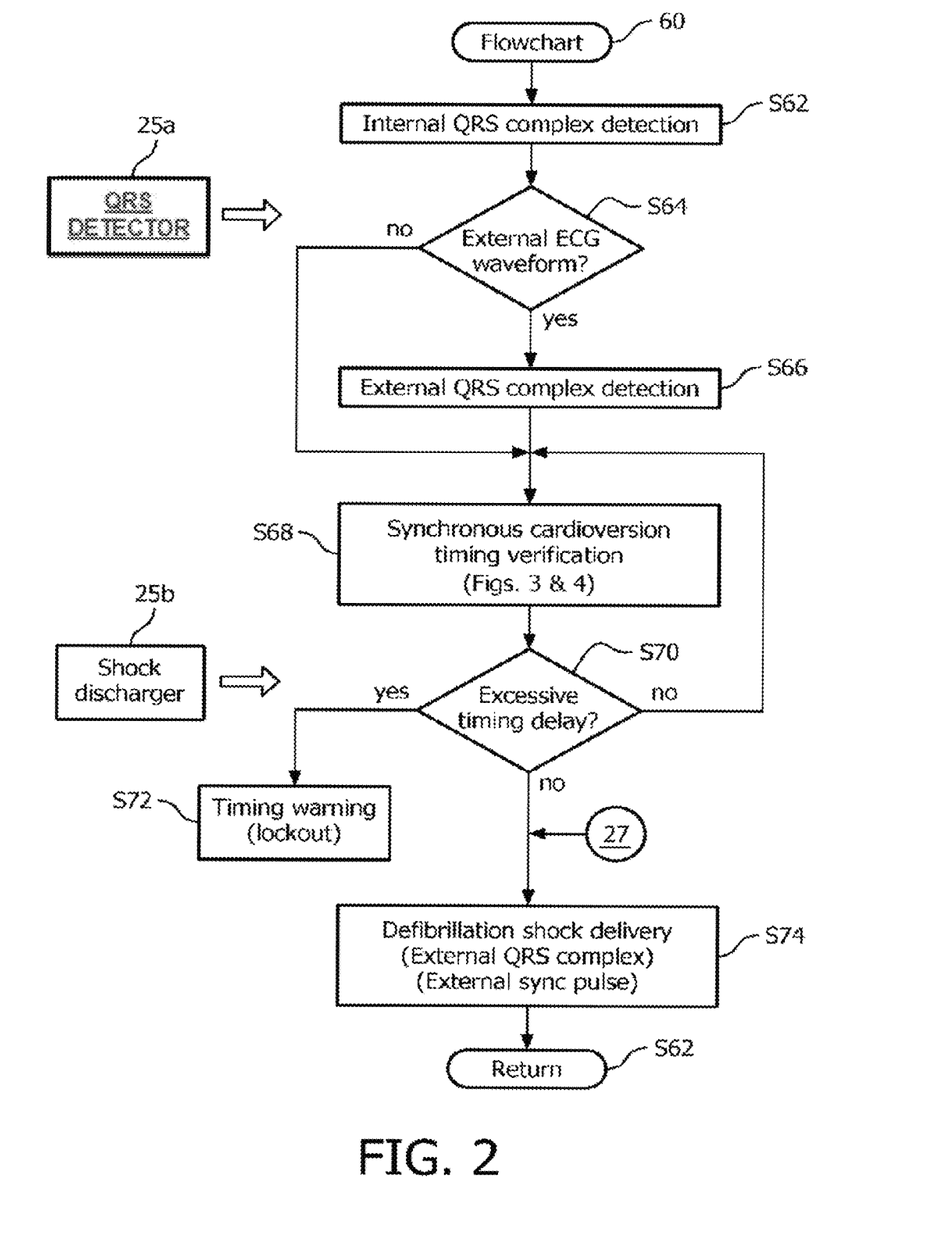
FIG. 2 illustrates a flowchart representative of an exemplary embodiment of a mixed mode/timing verification synchronized cardioversion method in accordance with the present invention.

Referring to FIG. 2, a flowchart 60 representative of the synchronized cardioversion method of the present invention executable by controller 25. The following is a description of an execution of flowchart 60 by a QRS detector 25*a* and a shock discharger 25*b* of controller 25. Please note a pressing of charge button 26 activates a storage of electric energy by shock source 24 (FIG. 1), preferably by a charging of a high voltage capacitor bank, and a pressing of shock button 27 activates a synchronized cardioversion by defibrillator 20, which may only be activated upon an arming of defibrillator 20.

A stage S62 of flowchart 60 encompasses QRS detector 25*a* executing a detection of each QRS complex of the ECG waveform 50 provided by internal ECG monitor 23 and a stage S64 of flowchart 60 encompasses QRS detector 25*a* determining whether external ECG waveform 50 or synchronized pulse 51 is being applied to input channel 29 by external ECG monitor 40. For this determination, QRS detector 25*a* attempts to detect an equivalence or nonequivalence of a pulse profile 32 to the synchronized cardioversion signal.

In one embodiment, QRS detector 25*a* looks for a rising edge of a square pulse of the synchronized cardioversion signal prior to low pass filter of the input signal. QRS detector 25*a* deems the input signal to be a synchronizing pulse signal 51 if (1) an amplitude of a rising edge of the input signal is equal to or greater than an amplitude of a rising edge of the pulse profile, (2) a rise time of the rising edge of the input signal is equal to or greater than a rise time of the pulse profile, and (3) a duration of the input signal is equal to or greater than a duration of the pulse profile (e.g., a maximum expected duration of a pacemaker pulse for patients that might have an implanted pacemaker). Otherwise, QRS detector 25*a* deems the input signal to be an external ECG waveform 50 and proceeds to a stage S66 of flowchart 60 to execute a detection of each QRS complex of external ECG waveform 50 applied to input channel 29.

For example, as shown in FIG. 1, QRS detector 25*a* would deem the input signal to be synchronizing pulse signal 51 in view of (1) an amplitude of a rising edge of synchronizing pulse signal 51 being greater than an amplitude of a rising edge of the pulse profile 32, (2) a rise time of the rising edge of synchronizing pulse signal 51 being greater than a rise time of pulse profile 32, and (3) a duration of the synchronizing pulse signal 51 being equal to or greater than the duration of pulse profile 32.

Otherwise, as shown in FIG. 1, QRS detector 25*a* would deem the input signal to be external ECG waveform 50 in view of (1) an amplitude of a rising edge of the external ECG waveform 50 being less than an amplitude of a rising edge of pulse profile 32, or (2) the rise time of the leading edge of external ECG waveform 50 being less than a rise time of the leading edge of pulse profile 32, or (3) the duration of external ECG waveform 50 being less than a duration of pulse profile 32. More particularly, the duration of pulse profile 32 is specifically needed to avoid an implanted pacemaker pulse (durations up to 2 milliseconds) from being seen by QRS detector 25*a* as a synchronizing pulse. QRS detector 25*a* is therefore configured on how an external ECG monitor 40 may represent a pacemaker pulse, which could increase the duration to about 6 milliseconds. Thus, by example, if the pulse duration requirement was set to 8 milliseconds, then QRS detector 25*a* could accurately determine if the input signal was a pulse or waveform for patient 10 having an implanted pacemaker.

Referring back to FIG. 2, prior to arming of shock button 27, the QRS complex detection of stage S62 is a continual process and the QRS complex detection of stage S66 is a continual process if external ECG waveform 50 was detected at ECG input 29. While the process(es) are being executed by QRS detector 25*a*, shock discharger 25*b* executes stages S68-S72 of flowchart 60 as needed to ensure a timing delay between the QRS complex detection process of stage S62 and the receipt of the synchronized cardioversion input signal at channel 29 is not excessive.

Specifically, stage S68 encompasses shock discharger 25*b* executing a timing verification involving a comparison of a baseline time delay to a measured time delay to determine if the measured time delay is excessive during stage S70. The baseline time delay is an acceptable added time delay to a normal time of an internal QRS complex detection of stage S68 and a delivery of a synchronized shock to patient 10 that would still comply with the overall sixty (60) millisecond requirement for synchronized cardioversion.

Figure 3:
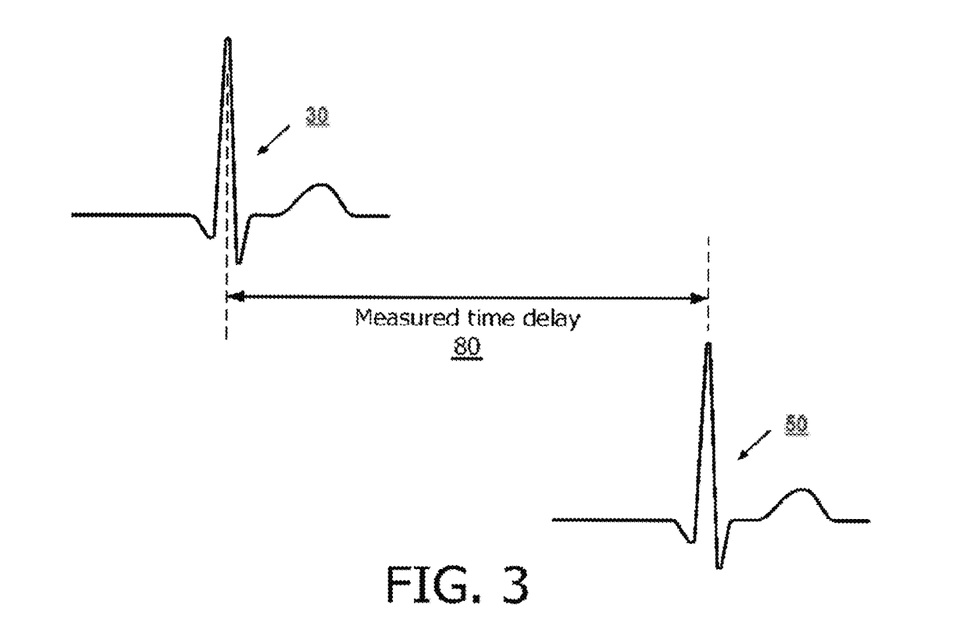
FIGS. 3 and 4 illustrate exemplary examples of time delay verifications in accordance with the present invention.

In one embodiment of stage 68 as shown in FIG. 3 for the external ECG waveform 50 being applied to ECG input 29, the baseline time delay is compared to a measured time delay 80 between a detection of a R peak of ECG waveform 30 by QRS detector 25a and a detection of a R peak of ECG waveform 50 by QRS detector 25a.

Figure 4:
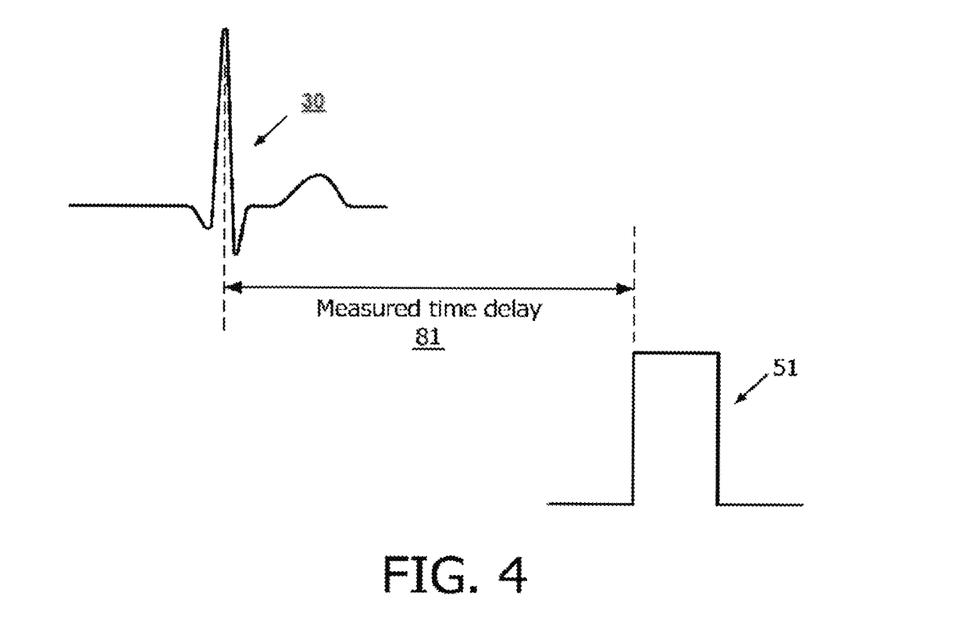

In a second embodiment of stage 68 as shown in FIG. 4 for the synchronized pulse signal 51 being applied to ECG input 29, the baseline time delay is compared to a measured time delay 81 between a detection of a QRS complex of ECG waveform 30 by QRS detector 25a and a detection of synchronized pulse signal 51 by QRS detector 25a.

If shock discharger 25b determines the measured time delay is excessive during stage S70 (i.e., the measured time delay is greater than the baseline time delay), then shock discharger 25b proceeds to stage S72 to communicate a time delay warning that preferably includes a lockout of shock button 27 to prohibit any delivery of a defibrillation shock.

If shock discharger 25b determines that the measured time delay is not excessive during stage S70 (i.e., the measured time delay is less than the baseline time delay), then shock discharger 25b continues to a loop of stage S68 and S70 until such time the measured time delay becomes excessive or shock button 27 is pressed.

If shock button 27 is pressed, then a stage S74 of flowchart 70 encompasses shock discharger 25b delivering the defibrillation shock to patient 10. If synchronizing pulse signal 51 was detected at stage S64, then a detection output of QRS detector 25a for triggering the shock is disabled for the duration of pulse 51 up to a maximum duration of an acceptable synchronizing pulse and shock discharger 25b synchronizes the defibrillation shock to pulse 51. Otherwise, the detection output of QRS detector 25a for triggering the shock is enabled and shock discharger 25b synchronizes the defibrillation shock to the detection output of QRS detector based on external ECG waveform 50.

Referring to FIG. 2, stages S64-66 and S74 represent a mixed mode operation of the present invention and stages S64, S68-S74 represent a timing verification of the present invention. In practice, the mixed mode operation and/or the timing verification may be individually executed or individually incorporated in other methods of delivering a defibrillation shock to a patient.

Also in practice, shock discharger 25b may execute stages S68-S72 on behalf of an external ECG monitor exclusively applying either an ECG waveform or a synchronized pulse to input channel 29.

From the description of FIG. 2, conditions for delivering the defibrillation shock to the patient include, but are not limited, to (1) the defibrillator receiving and detecting the synchronized cardioversion input signal is the external ECG data and detecting at least one QRS complex within the external ECG data, particularly without any excessive time delay due to the defibrillator receiving the external ECG data and detecting the at least one QRS complex, and (2) the defibrillator receiving and detecting the synchronized cardioversion input signal is the synchronized pulse, particularly without any excessive time delay in receiving and detecting the synchronized pulse.

Referring to FIGS. 1-4, those having ordinary skill in the art will appreciate numerous benefits of the present invention including, but not limited to, (1) minimizing a risk that a clinician can incorrectly configure synchronized cardioversion on a defibrillator using an external ECG monitor, (2) simplification of defibrillator design by providing only one input for external controlled synchronized cardioversion involving a synchronizing pulse and standard ECG signal to thereby prevent any confusion of the clinician with two different connectors for the two different inputs, and (3) minimizing a risk that the clinician can incorrectly deliver a shock on the T wave which could cause ventricular fibrillation when using an external ECG monitor output for synchronizing the shock by alerting the clinician if the delay from the external ECG monitor is excessive.

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. A defibrillator, for a synchronized cardioversion mixed mode operation with an external ECG monitor located external to the defibrillator, the defibrillator comprising:
    a shock source configured to store electric energy; and
    a controller including a synchronized cardioversion input channel for receiving a synchronized cardioversion input signal from the external ECG monitor,
        wherein the synchronized cardioversion input signal is one of an external ECG waveform of a heart of a patient generated by the external ECG monitor or an external synchronized pulse generated by the external ECG monitor as an indication of a detection by the external ECG monitor of at least one QRS complex of the external ECG waveform,
        wherein the controller is configured to control a first conditional delivery of a defibrillation shock synchronized with the synchronized cardioversion input signal by the shock source to the patient in response to the controller receiving the synchronized cardioversion input signal as the external ECG waveform, and
        wherein the controller is configured to control a second conditional delivery of a defibrillation shock synchronized with the synchronized cardioversion input signal by the shock source to the patient in response to the controller receiving the synchronized cardioversion input signal as the external synchronized pulse.

2. The defibrillator of claim 1, wherein the controller is further configured to:
    detect the synchronized cardioversion input signal is the external ECG waveform in response to the synchronized cardioversion input signal being nonequivalent to a pulse profile; and
    detect the synchronized cardioversion input signal is the external synchronized pulse in response to the synchronized cardioversion input signal being equivalent to the pulse profile.

3. The defibrillator of claim 2, wherein the pulse profile has at least one an amplitude, a rise time and a duration defining a baseline synchronized pulse signal.

4. The defibrillator of claim 2, wherein the synchronized cardioversion input signal is equivalent to the pulse profile in response to at least one of:
   an amplitude of the external synchronized pulse signal being equal to or greater than an amplitude of the pulse profile,
   a rise time of the external synchronized pulse signal being equal to or greater than a rise time of the pulse profile, and
   a duration of the external synchronized pulse signal being equal to or greater than a duration of the pulse profile.

5. The defibrillator of claim 1,
   wherein the controller is further configured to detect the at least one QRS complex within the external ECG waveform in response to the synchronized cardioversion input signal being the external ECG waveform; and
   wherein the shock source delivers the defibrillation shock synchronized with the synchronized cardioversion input signal to the patient in response to the controller detecting the at least one QRS complex of the external ECG waveform.

6. The defibrillator of claim 1, further comprising:
   an ECG monitor internal to the defibrillator,
      wherein the internal ECG monitor is configured to generate an internal ECG waveform of the heart of the patient; and
   wherein the controller is further configured to:
      detect at least one QRS complex of the internal ECG waveform and of the at least one QRS complex of the external ECG waveform in response to the synchronized cardioversion input signal being the external ECG waveform;
      measure a time delay between the internal ECG waveform and the external ECG waveform; and
      control a delivery by the shock source of the defibrillation shock synchronized with the synchronized cardioversion input signal to the patient in response to the measured time delay between the internal ECG waveform and the external ECG waveform being less than a baseline time delay.

7. The defibrillator of claim 1, further comprising:
   an ECG monitor internal to the defibrillator,
      wherein the internal ECG monitor is configured to generate an internal ECG waveform of the heart of the patient; and
   wherein the controller is further configured to:
      detect at least one QRS complex of the internal ECG waveform and of the at least one QRS complex of the external ECG waveform in response to the synchronized cardioversion input signal being the external ECG waveform;
      measure a time delay between the internal ECG waveform and the external ECG waveform; and
      control at least one of a warning or a prohibition of a delivery by the shock source of the defibrillation shock synchronized with the synchronized cardioversion input signal to the patient in response to the measured time delay between the internal ECG waveform and the external ECG waveform being greater than a baseline time delay.

8. The defibrillator of claim 1, wherein a condition of the second conditional delivery is the synchronized cardioversion input signal is the external synchronized pulse.

9. The defibrillator of claim 1, further comprising:
   an ECG monitor internal to the defibrillator,
      wherein the internal ECG monitor is configured to generate an internal ECG waveform of the heart of the patient; and
   wherein the controller is further configured to:
      detect at least one QRS complex of the internal ECG waveform in response to the synchronized cardioversion input signal being the external synchronized pulse;
      measure a time delay between the internal ECG waveform and the external synchronized pulse; and
      control a delivery by the shock source of the defibrillation shock synchronized with the synchronized cardioversion input signal to the patient in response to the measured time delay between the internal ECG waveform and the external synchronized pulse being less than a baseline time delay.

10. The defibrillator of claim 1, further comprising:
    an ECG monitor internal to the defibrillator,
       wherein the internal ECG monitor is configured to generate an internal ECG waveform of the heart of the patient; and
    wherein the controller is further structurally configured to:
       detect at least one QRS complex of the internal ECG waveform in response to the synchronized cardioversion input signal being the external synchronized pulse;
       measure a time delay between the internal ECG waveform and the external synchronized pulse; and
       control at least one of a warning or a prohibition of a delivery by the shock source of the defibrillation shock synchronized with the synchronized cardioversion input signal to the patient in response to the measured time delay between the internal ECG waveform and external synchronized pulse being greater than a baseline time delay.

11. A defibrillator system, comprising:
    an external ECG monitor configured to generate an external ECG waveform of a heart of a patient and an external synchronized pulse as an indication of a detection by the external ECG monitor of at least one QRS complex of the external ECG waveform; and
    a defibrillator for a synchronized cardioversion mixed mode operation with the external ECG monitor located external to the defibrillator,
       wherein the defibrillator includes a synchronized cardioversion input channel for receiving a synchronized cardioversion input signal from the external ECG monitor,
       wherein the synchronized cardioversion input signal is one of the external ECG waveform or the external synchronized pulse,
       wherein the defibrillator is configured to control a first conditional delivery of a defibrillation shock synchronized with the synchronized cardioversion input signal to the patient in response to the defibrillator receiving the synchronized cardioversion input signal as the external ECG waveform, and
       wherein the defibrillator is configured to control a second conditional delivery of a defibrillation shock synchronized with the synchronized cardioversion input signal to the patient in response to the defibrillator receiving the synchronized cardioversion input signal as the external synchronized pulse.

12. The defibrillation system of claim 11, wherein the defibrillator is further structurally configured to:

detect the synchronized cardioversion input signal is the external ECG waveform in response to the synchronized cardioversion input signal being nonequivalent to a pulse profile; and detect the synchronized cardioversion input signal is the external synchronized pulse in response to the synchronized cardioversion input signal being equivalent to the pulse profile.

13. The defibrillation system of claim 11, wherein the defibrillator is further configured to:

generate an internal ECG waveform of the heart of the patient;

measure a time delay between the internal ECG waveform and the synchronized cardioversion input signal; and control a delivery of the defibrillation shock synchronized with the synchronized cardioversion input signal to the patient in response to the measured time delay between the internal ECG waveform and the synchronized cardioversion input signal being less than a baseline time delay.

14. The defibrillation system of claim 11, wherein the defibrillator is further configured to:

generate an internal ECG waveform of the heart of the patient;

measure a time delay between the internal ECG waveform and the synchronized cardioversion input signal; and execute at least one of a warning and a prohibition of a delivery of the defibrillation shock synchronized with the synchronized cardioversion input signal to the patient in response to the measured time delay between the internal ECG waveform and the synchronized cardioversion input signal being greater than a baseline time delay.

15. The defibrillation system of claim 14, wherein the synchronized cardioversion input signal is equivalent to a pulse profile in response to at least one of:

an amplitude of the external synchronized pulse signal being equal to or greater than an amplitude of the pulse profile, a rise time of the external synchronized pulse signal being equal to or greater than a rise time of the pulse profile, and a duration of the external synchronized pulse signal being equal to or greater than a duration of the pulse profile.

16. A method for a synchronized cardioversion mixed mode operation by a defibrillator with an external ECG monitor located external to the defibrillator, the method comprising:

the defibrillator receiving a synchronized cardioversion input signal from the external ECG monitor through a synchronized cardioversion input channel, wherein the synchronized cardioversion input signal is one of external ECG waveform of a heart of a patient generated by the external ECG monitor or an external synchronized pulse generated by the ECG monitor as an indication of a detection by the external ECG monitor of at least one QRS complex of the external ECG waveform;

the defibrillator controlling a first conditional delivery of a defibrillation shock synchronized with the synchronized cardioversion input signal to the patient in response to the defibrillator receiving the synchronized cardioversion input signal as the external ECG waveform; and the defibrillator controlling a second conditional delivery of the defibrillation shock synchronized with the synchronized cardioversion input signal to the patient in response to the defibrillator receiving the synchronized cardioversion input signal as the external synchronized pulse.

17. The method of claim 16, further comprising:

the defibrillator detecting the synchronized cardioversion input signal is the external ECG waveform in response to the synchronized cardioversion input signal being nonequivalent to a pulse profile; and the defibrillator detecting the synchronized cardioversion input signal is the external synchronized pulse in response to the synchronized cardioversion input signal being equivalent to the pulse profile.

18. The method of claim 17, wherein the synchronized cardioversion input signal is equivalent to the pulse profile in response to at least one of:

an amplitude of the external synchronized pulse signal being equal to or greater than ah amplitude of the pulse profile, a rise time of the external synchronized pulse signal being equal to or greater than a rise time of the pulse profile, and a duration of the external synchronized pulse signal being equal to or greater than a duration of the pulse profile.

19. The method of claim 16, further comprising:

the defibrillator generating an internal ECG waveform of the heart of the patient;

the defibrillator measuring a time delay between the internal ECG waveform and the synchronized cardioversion input signal; and the defibrillator controlling a delivery of the defibrillation shock synchronized with the synchronized cardioversion input signal to the patient in response to the measured time delay between the internal ECG waveform and the synchronized cardioversion input signal being less than a baseline time delay.

20. The method of claim 16, further comprising:

the defibrillator generating an internal ECG waveform of the heart of the patient;

the defibrillator measuring a time delay between the internal ECG waveform and the synchronized cardioversion input signal; and the defibrillator controlling at least one of a warning and a prohibition of a delivery of the defibrillation shock synchronized with the synchronized cardioversion input signal to the patient in response to the measured time delay between the internal ECG waveform and the synchronized cardioversion input signal being greater than a baseline time delay.

* * * * *